United States Patent [19]

Rardon et al.

[11] Patent Number: 5,545,696
[45] Date of Patent: Aug. 13, 1996

[54] ETHERIFIED ALKYL OR ARYLCARBAMYLMETHYLATED AMINOTRIAZINES AND CURABLE COMPOSITIONS CONTAINING THE SAME

[75] Inventors: Daniel E. Rardon, Pittsburgh; Gregory J. McCollum, Gibsonia, both of Pa.

[73] Assignee: PPG Industries, Inc., Pittsburgh, Pa.

[21] Appl. No.: 454,787

[22] Filed: May 31, 1995

Related U.S. Application Data

[62] Division of Ser. No. 157,456, Nov. 26, 1993.

[51] Int. Cl.$^6$ ............................................. C08F 8/32
[52] U.S. Cl. .................. 525/375; 525/328.8; 525/437; 525/454; 525/533
[58] Field of Search .......................... 525/375, 437, 525/454, 533

[56] References Cited

U.S. PATENT DOCUMENTS

| | | | |
|---|---|---|---|
| 4,031,050 | 6/1977 | Jerabek | 260/29.2 TN |
| 4,708,984 | 11/1987 | Forgione et al. | 525/127 |
| 4,710,542 | 12/1987 | Forgione et al. | 525/127 |
| 4,913,972 | 4/1990 | Grunewalder et al. | 428/425.5 |
| 5,300,328 | 4/1994 | Rehfuss | 427/388.3 |

OTHER PUBLICATIONS

Organic Coatings Science and Technology, XV, pp. 379–393 (1989).

*Primary Examiner*—Bernard Lipman
*Attorney, Agent, or Firm*—William J. Uhl; Kenneth J. Stachel

[57] ABSTRACT

Novel carbamyl-methylated aminotriazines and curable compositions comprising these aminotriazines are disclosed. The carbamyl-methylated aminotriazines are substituted with derivatives of monoalkyl ethers and/or monoaryl ethers of alkylene glycols. The curable compositions are particularly useful as film formers in coatings.

8 Claims, No Drawings

ETHERIFIED ALKYL OR ARYLCARBAMYLMETHYLATED AMINOTRIAZINES AND CURABLE COMPOSITIONS CONTAINING THE SAME

This is a divisional of U.S. patent application Ser. No. 08/157,456, filed Nov. 26, 1993

FIELD OF THE INVENTION

The present invention relates to novel triazines and to curable compositions containing such materials. More particularly, the present invention relates to novel carbamylmethylated aminotriazines and to curable compositions comprising these novel aminotriazines.

BACKGROUND OF THE INVENTION

The incorporation and use of carbamyl-substituted aminotriazines in curable compositions is known in prior art. For example, see U.S. Pat. No. 4,708,984, and U.S. Pat. No. 4,710,542.

The above compositions, for the most part, have limited compatibility with organic solvents and often require formulations with high solvent contents. Additionally, the coatings deposited with such compositions often give cured films which are deficient in coating properties such as gloss, flow, flexibility and impact resistance. Also, such coatings require a high curing temperature of 232° C. or higher.

The present invention overcomes certain of the above shortcomings by providing novel carbamylmethylated aminotriazines which, when formulated into curable compositions, provide coatings with good gloss and flow characteristics, are hard yet flexible and have good impact resistance. Coatings made with such compositions can be prepared with relatively low curing temperatures of 176° C. or lower. Additionally, the novel compositions offer a broad range of compatibility with organic solvents, and coatings formulations with low solvent contents can be formulated. The novel compositions can also be formulated as aqueous dispersions which can be used in electrodeposition applications.

SUMMARY OF THE INVENTION

According to the present invention, there are provided triazines selected from the group consisting of
(i) a triaminotriazine compound of the formula

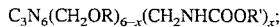

(ii) a benzoguanamine compound of the formula

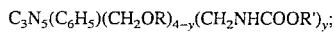

(iii) an oligomer of (i) or of (ii);
(iv) mixtures among various members of (i), (ii) and (iii) wherein the R and R' are independently radicals derived from monoalkyl ethers of alkylene glycols having at least 4 carbon atoms and monoaryl ethers of alkylene glycols having at least 8 carbon atoms; alone or combined with alkyl groups having 1 to 20 carbon atoms where x is in the range of from about 2 to about 6, and y is in the range of from about 2 to about 4.

Also contemplated by the present invention are curable compositions comprising the triazines described above and an active hydrogen-containing material.

Coatings deposited from these compositions upon curing possess good gloss and flow characteristics as well as good flexibility and impact resistance while providing hard films. Such coatings will have the added benefit of low curing temperatures and offer a broad range of compatibility with organic solvents. In addition, coatings formulations with low solvent contents can be obtained. The compositions can be dispersed in aqueous medium to form aqueous-based coating compositions. Such properties make these compositions well suited for use in coil coatings, extrusion coatings, can coatings and electrodeposition coatings.

DETAILED DESCRIPTION OF THE INVENTION

The preferred embodiments of invention are triaminotriazines of the formula $C_3N_6(CH_2OR)_{6-x}(CH_2NHCOOR')_x$ and of the benzoguanamine formula

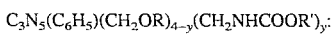

R and R' are independently radicals derived from monoalkyl ethers of alkylene (including polyalkylene) glycols having at least 4, more preferably 4–12 carbon atoms and monoaryl ethers of alkylene (including polyalkylene) glycols having at least 8, preferably ! from 8–12 carbon atoms. For example, in the case of the monomethyl ether of propylene glycol, R and R' are

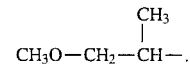

In the case of the monophenyl ether of diethylene glycol, R and R' are

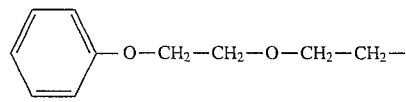

Thus, R and R' are alkoxy substituted alkylene (including alkylene oxy groups) and aryloxy substituted alkylene (including alkylene oxy) groups. Preferably, the alkoxy group contains 1 to 10 carbon atoms, the aryloxy group contains 6 to 10 carbon atoms and the alkylene (including the alkylene oxy group) contains 2 to 6 carbon atoms.

Preferably, X is in the range of about 3 to 6 carbon atoms, and y is in the range of about 3 to 4 carbon atoms.

Preferred alkylene glycols are ethylene glycol, propylene glycol, diethylene glycol and dipropylene glycol.

Preferred monoaryl and monoalkyl substituents are phenyl, methyl, propyl, butyl and hexyl groups.

R and R' can be mixed groups and can also include alkyl groups of about 1 to 20 carbon atoms. Preferred alkyl substituents are of 1–4 carbon atoms, such as methyl and butyl groups.

As starting materials to produce the alkyl or aryl carbamylmethylated triazines of this invention, there can be used hydroxymethyl or alkoxymethyl melamines and/or benzoguanamines and oligomers thereof known in the art. Many of these starting materials are commercially available or can be made by well known procedures.

The melamine or benzoguanamine compounds are reacted with glycol ether carbamates, such as methoxypropyl carbamate and butoxyethyl carbamate, alone or in combination with alcohols and alkylcarbamates. The glycol ether carbamates are prepared by reacting glycol ethers, such as the monoalkyl and monoaryl ethers of alkylene glycols such as those mentioned above, with urea in the presence of a transesterification catalyst such as tin, nickel or lead by methods well known in the art.

An idealized reaction equation for the preparation of the new compounds from an alkoxymethylmelamine or a hydroxymethylmelamine and glycol ether carbamates is as follows:

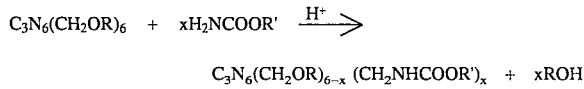

$$C_3N_6(CH_2OR)_{6-x}(CH_2NHCOOR')_x + xROH$$

wherein R, R' and x are defined above.

The mole ratio of melamine compound to glycol ether carbamate is selected to provide the desired degree of substitution. Preferably, from 3 to 6 moles of glycol ether carbamate can be used per 1 mole of melamine compound. If less than 3 moles of carbamate are used, per mole of melamine compound, premature gelation can be a problem. This chemical reaction is typically carried out by heating in the melt or in solution.

With the benzoguanamine starting material, the preferred mole ratio of glycol ether carbamate to benzoguanamine starting material is 3 to 4/1 (i.e. y=3–4 for the benzoguanamine compound shown in the structural formula).

The reaction temperature can range from 70° to 125° C. The preferred temperature range is 95° to 115° C. The quantity of alcohol (ROH) evolved gives an indication of reaction completion. An acid catalyst such as methane sulfuric acid is usually present during the reaction.

With 6 moles of glycol ether carbamate, the reaction is usually not 100% complete unless forced. However, a high degree of substitution, x=5–6; (y=3–4 with the benzoguanamine compound) is obtained.

Preferably reaction is conducted in the presence of a high boiling alcohol such as methoxy propanol and butoxyethanol which bring about an etherification or transetherification reaction with the starting melamine or benzoguanamine compound. It is noted that the resulting carbamylmethyl aminotriazine-products tend to be oligomeric. Gel permeation chromatography typically indicates the majority of the product is comprised of a distribution of oligomers.

The triazines of the present invention can be used in combination with active hydrogen-containing materials, which are well known in the art, to form curable compositions.

The active hydrogen-containing materials can have as the active hydrogen group a group selected from carboxylic acid hydroxy, amino (i.e. primary amine, secondary amine (including imine)), amido, and thiol including mixtures of such groups. The active hydrogen-containing materials useful herein are typically film-forming compositions.

Examples of suitable active hydrogen-containing polymers are hydroxy functional acrylic polymer, hydroxy functional polyesters, hydroxy functional polyurethanes, hydroxy functional epoxy polymers and hydroxy functional epoxy-amine reaction product polymers including mixtures thereof.

Useful hydroxyl-containing acrylic polymers are described in U.S. Pat. No. 4,913,972, col. 16, line 63 to col. 4, line 47; hydroxy functional polyesters are described in U.S. Pat. No. 4,913,972, col. 16, lines 9–62; hydroxy functional polyurethanes are described in U.S. Pat. No. 4,913,972, col. 17, line 62 to col. 18, line 7 and col. 15, line 35 to col. 16, line 8; hydroxy functional epoxies are described in U.S. Pat. No. 4,913,972, col. 17, lines 38–61 and hydroxy functional epoxy amine reaction products are described in U.S. Pat. No. 4,031,050, col. 3, line 23 to col. 5, line 8.

These hydroxyl functional polymers typically have hydroxyl values of 50 to 400 on a resin solids basis.

Generally, the curable compositions described above will contain at least 5 and preferably 20 to 100, percent by weight of aminotriazine and active hydrogen-containing polymer based on total weight of the curable composition. Preferably, the weight ratio of aminotriazine to active hydrogen-containing material will range from about 5 to about 40 parts to correspondingly from 60 to 95 parts of the active hydrogen-containing material.

The curable compositions of the present invention can be solubilized or dispersed in organic solvents such as alcohols, esters, or water or mixtures thereof.

For solubilization or dispersion in water or mixtures of water and organic solvent, the polyester, polyurethane or acrylic polymers preferably contain carboxylic acid groups and are at least partially neutralized with amine to form anionic polymers. Epoxy-amine reaction product polymers can be neutralized with acid to form cationic polymers.

The curable composition typically includes a cure catalyst. The cure catalyst can be a metal salt and/or complex of a metal such as lead, zinc, iron, manganese, and preferably tin. Suitable salts of these metals are, for example, acetates, octoates, laurates and naphthenates. Specific examples include tetrabutyldiacetoxy distannoxane, dibutyltin dilaurate, dibutyltin oxide and tin acetyl acetonate complex.

The cure catalyst is used in amounts effective to accelerate cure at the temperatures employed, e.g., 120° to 400° C, preferably 150° to 360° C. for 30 seconds to 30 minutes. Typically, the catalyst is used in amounts from about 0.1 to about 2.0, preferably 0.2 to 1.7%, metal by solids weight based on the weight of the curable compositions.

Acid catalysts can also be used when the aminotriazine compounds of the present invention contain ether functional groups. Example of such catalysts include nitric acid, sulfuric acid, p-toluenesulfonic acid and the like. Where used, the acid catalyst is present in amounts of 0.1 to 2.0 percent by weight based on weight of the curable composition. Preferably, the combination of a tin catalyst and an acid catalyst is used.

Besides the above-mentioned ingredients, the compositions can optionally contain pigments and various conventional additives such as antioxidants, surface active agents, flow control agents and the like.

The following examples illustrate the triazines and curable compositions of the present invention and are not to be construed as limiting the claims unless otherwise indicated. All parts are by weight unless otherwise indicated.

EXAMPLE 1

Reaction Product of 6 Moles of Methoxypropyl Carbamate with 1 Mole of Hexamethoxymethylmelamine Oligomeric hexamethoxymethylmelamine (180.0 g, 0.46 mole, American Cyanamid Co. CYMEL 303), methoxypropyl carbamate (370.0 g, 2.78 mole), and methanesulfonic acid (1.10 g) are stirred at 100° C. in a flask equipped with a Dean Stark distillation trap and a nitrogen sparge inlet. Over 3 to 4 hours 64 g of methanol (72% of theoretical) are collected in the receiver. Methoxypropyl acetate (150 g, Dow Chemical Co, PM Acetate) is added and the temperature is increased to 115° C. at which time more methanol is collected. After cooling the reaction to 80° C., the acid is neutralized with dimethyl ethanolamine (1.10 g). Sufficient PM Acetate (75 g) is added to achieve a Gardner-Holdt viscosity of Z to Z1. The resulting clear, colorless resin (695 g) is measured at 73.9% total nonvolatiles (110° C., 60 minutes). Gas chromatographic analysis shows about 9% residual carbamate by peak area, corresponding to a slight excess of five (on average) methoxy groups being replaced by the methoxypropyl carbamate groups. The approximate formula is:

$$C_3N_6(CH_2OCH_3)_{0.1}(CH_2NHCOOCH(CH_3)CH_2OCH_3)_{5.6}$$

Gel permeation chromatography shows a fairly uniform distribution of oligomeric material (about 78%, $M_w$ 5476) and a single peak corresponding to monomeric material.

EXAMPLE 2

Reaction Product of 3 Moles of Methoxypropyl Carbamate and 2 Moles of Methoxypropanol with 1 Mole of Hexamethoxymethylmelamine Oligomeric hexamethoxymethylmelamine (200.0 g, 0.51 mole), methoxypropyl carbamate (205.0 g, 1.54 mole), methoxypropanol (137.0 g, 1.52 mole, Dow Chemical Co. DOWANOL PM), and methanesulfonic acid (1.00 g) are stirred at 100° C. in a flask equipped with a Dean Stark distillation receiver and a nitrogen sparge inlet. Over 3 hours 55 g of methanol (67% of theoretical base upon the number of moles of carbamate and hydroxyl present) is collected in the receiver. Dimethyl ethanolamine (1.00 g) is added to neutralize the acid catalyst. The resulting clear, colorless resin is measured at a Z Gardner-Holdt viscosity and 71.6% total nonvolatiles (110° C., 60 minutes). Gas chromatographic analysis shows <1% residual carbamate and about 25% residual DOWANOL PM meaning only a minimal amount of the secondary alcohol reacts. The approximate formula is:

$$C_3N_6(CH_2OCH_3)_{2.3}(CH_2NHCOOCH(CH_3)CH_2OCH_3)_3(CH_2OCH(CH_3)CH_2OCH_3)_{0.1}$$

Gel permeation chromatography shows a fairly uniform distribution of oligomeric material (about 70%, Mw 3200) and a single peak corresponding to monomeric material.

EXAMPLE 3

Reaction Product of 3 Moles of Methoxypropyl Carbamate with 1 Mole of Hexamethoxymethylmelamine in Excess 2-Butoxyethanol Oligomeric hexamethoxymethylmelamine (200.0 g, 0.51 mole), methoxypropyl carbamate (205 g, 1.54 mole), 2-butoxyethanol (250.0 g, 2.12 mole, Union Carbide Co. Butyl CELLOSOLVE), and dodecylbenzenesulfonic acid (2.60 g, 70%) are stirred at 110° C. in a flask equipped with a Dean Stark distillation receiver and a nitrogen sparge inlet. Over 3.5 hours 70 g of methanol (87% based upon six reactive sites) is collected in the receiver, and the acid catalyst is neutralized with dimethyl ethanolamine (2.60 g). The flask is then fitted with a vacuum distillation receiver, and the pressure is slowly reduced to 100 mm Hg to distill a portion of the butyl CELLOSOLVE. About 50 g of distillate is collected, and the resulting clear, slightly yellow resin is measured at a Z1 Gardner-Holdt viscosity and 75.8% total nonvolatiles (110° C., 60 minutes). Gas chromatographic analysis shows <1% residual carbamate. The approximate formula is:

$$C_3N_6(CH_2OCH_3)_{0.3}(CH_2NHCOOCH(CH_3)CH_2OCH_3)_3(CH_2OCH_2CH_2OCH_3)_{0.3}$$

Gel permeation chromatography shows a fairly uniform distribution of oligomeric material (about 75%, Mw 2230) and a single peak corresponding to monomeric material.

EXAMPLE 4

Reaction Product of 5 Moles of Butoxypropyl Carbamate with 1 Mole of Hexamethoxymethylmelamine Oligomeric hexamethoxymethylmelamine (445.0 g, 1.14 mole), butoxypropyl carbamate (1000.0 g, 5.7 mole), and methanesulfonic acid (1.50 g) are stirred at 100° C. in a flask equipped with a Dean Stark distillation receiver and a nitrogen sparge inlet. Over 2 hours 120 g of methanol (66% of theoretical) is collected in the receiver. PM Acetate (250 g) is added and the temperature is increased to 115° C. at which time 20 g more methanol is collected (77% total). Sufficient PM Acetate (50 g) is added to achieve a Gardner-Holdt viscosity of Z1. The resulting clear, pale yellow resin (1545 g) is measured at 68.0% total nonvolatiles (110° C., 60 minutes). Gas The chromatographic analysis shows <1% residual carbamate. The approximate formula is:

$$C_3N_6(CH_2OCH_3)(CH_2NHCOOCH(CH_3)CH_2OC_4H_9)_5$$

Gel permeation chromatography shows a uniform distribution of oligomeric material (about 75%, Mw 6027) and a single peak corresponding to monomeric material.

EXAMPLE 5

Reaction Product of 5 Moles of Propoxypropyl Carbamate with 1 Mole of Hexamethoxymethylmelamine Oligomeric hexamethoxymethylmelamine (295.0 g, 0.76 mole), propoxypropyl carbamate (620.0 g, 3.8 mole), and methanesulfonic acid (1.80 g) are stirred at 100° C. in a flask equipped with a Dean Stark distillation receiver and a nitrogen sparge inlet. Over 4 hours 75 g of methanol (63% of theoretical) are collected in the receiver. PM Acetate (100 g) is added and the temperature is increased to 115° C. at which time 25 g more methanol is collected (83% total). Sufficient PM Acetate (100 g) is added to achieve a Gardner-Holdt viscosity of Y. The resulting clear, pale yellow resin is measured at 67.0% total nonvolatiles. Gas chromatographic analysis shows <1% residual carbamate. The approximate formula is:

$$C_3N_6(CH_2OCH_3)_1(CH_2NHCOOCH(CH_3)CH_2OC_3H_7)_5$$

EXAMPLE 6

Reaction Product of 6 Moles of 2-Butoxyethyl Carbamate with 1 Mole of Hexamethoxymethylmelamine Oligomeric hexamethoxymethylmelamine (121.0 g, 0.31 mole), 2-butoxyethyl carbamate (300.0 g, 1.36 mole), and methanesulfonic acid (0.34 g) are stirred at 100° C. in a flask equipped with a Dean Stark distillation trap and a nitrogen sparge inlet. Over 4 hours 35 g of methanol (62% of theoretical) are collected in the receiver. Butyl CELLOSOLVE (75 g) is added and 10 g more methanol (79% total)

is collected over 2 hours. The resulting clear, amber resin is measured at 77.1% total nonvolatiles (110° C., 60 minutes) with a Gardner-Holdt viscosity of Z. Gas chromatographic analysis shows about 9% residual carbamate corresponding to a slight excess of five (on average) methoxy groups being replaced by carbamate groups. The approximate formula is:

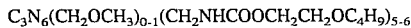
$C_3N_6(CH_2OCH_3)_{0-1}(CH_2NHCOOCH_2CH_2OC_4H_9)_{5-6}$

EXAMPLE 7

Reaction Product of 3 Moles of 2-Butoxyethyl Carbamate with 1 Mole of Hexamethoxymethylmelamine Oligomeric hexamethoxymethylmelamine (160.0 g, 0.41 mole), 2-butoxyethyl carbamate (200.0 g, 1.24 mole), and para-toluenesulfonic acid (0.72 g) are stirred at 100° C. in a flask equipped with a Dean Stark distillation receiver and a nitrogen sparge inlet. Over 5 hours 35 g of methanol (90% of theoretical) are collected in the receiver. Butyl CELLOSOLVE (100 g) is added to achieve a Gardner-Holdt viscosity of Z1. The resulting clear, yellow resin is measured at 81.4% total nonvolatiles (110° C., 60 minutes). The approximate formula is:

$C_3N_6(CH_2OCH_3)_3(CH_2NHCOOCH_2CH_2OC_4H_9)_3$

EXAMPLE 8

Reaction Product of 6 Moles of Diethylene Glycol Butyl Ether Carbamate with 1 Mole of Hexamethoxymethylmelamine Oligomeric hexamethoxymethylmelamine (200.0 g, 0.51 mole), diethylene glycol butyl ether carbamate (630.0 g, 3.06 mole), and methanesulfonic acid (2.0 g) are stirred at 110° C. in a flask equipped with a Dean Stark distillation receiver and a nitrogen sparge inlet. Over 6 hours 85 g of methanol are collected (89% of theoretical) in the receiver. The resulting yellow resin is measured at 92.0% total nonvolatiles (110° C., 60 minutes) with a Gardner-Holdt viscosity of Z4. The approximate formula is:

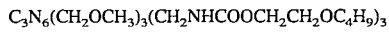
$C_3N_6(CH_2OCH_3)_{0-1}(CH_2NHCOOCH_2CH_2OCH_2CH_2OC_4H_9)_{5-6}$

EXAMPLE 9

Reaction Product of 3 Moles of Diethylene Glycol Butyl Ether Carbamate with 1 Mole of Hexamethoxymethylmelamine Oligomeric hexamethoxymethylmelamine (185.0 g, 0.47 mole), diethylene glycol butyl ether carbamate (300.0 g, 1.46 mole), and methanesulfonic acid (0.50 g) are stirred at 95° C. in a flask equipped with a Dean Stark distillation receiver and a nitrogen sparge inlet. Over 4 hours 40 g of methanol (89% of theoretical) are collected in the receiver. The resulting yellow resin is measured at 98% total nonvolatiles (110° C., 60 minutes) with a Gardner-Holdt viscosity of Z2. Gas chromatographic analysis shows no residual carbamate. The approximate formula is:

$C_3N_6(CH_2OCH_3)_3(CH_2NHCOOCH_2CH_2OCH_2CH_2OC_4H_9)_3$

EXAMPLE 10

Reaction Product of 5 Moles of Diethylene Glycol Butyl Ether Carbamate with 1 Mole of Hexamethoxymethylmelamine in Diethylene Glycol Monobutyl Ether Oligomeric hexamethoxymethylmelamine (120.0 g, 0.31 mole), diethylene glycol butyl ether carbamate (320.0 g, 1.55 mole), diethylene glycol monobutyl ether (130.0 g, 0.80 mole, Union Carbide Co., Butyl CARBITOL), and methanesulfonic acid (1.40 g) are stirred at 115° C. in a flask equipped with a Dean Stark distillation receiver and a nitrogen sparge inlet. Over 3.5 hours 42 g of methanol (86% of theoretical) are collected in the receiver, at which time dimethyl ethanolamine (1.40 g) is added to neutralize the acid catalyst. The resulting pale yellow resin is filtered and is measured at 81.4% total nonvolatiles with a Gardner-Holdt viscosity of V. Gas chromatographic analysis shows <1% residual carbamate. The approximate formula is:

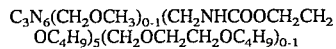
$C_3N_6(CH_2OCH_3)_{0-1}(CH_2NHCOOCH_2CH_2OC_4H_9)_5(CH_2OCH_2CH_2OC_4H_9)_{0-1}$ Gel permeation chromatography shows a uniform distribution of oligomeric material (about 85%, Mw 8459) and a single peak corresponding to monomeric material.

EXAMPLE 11

Reaction Product of 5 Moles of Dipropylene Glycol Methyl Ether Carbamate with 1 Mole of Hexamethoxymethylmelamine Oligomeric hexamethoxymethylmelamine (164.0 g, 0.42 mole), dipropylene glycol methyl ether carbamate (400.0 g, 2.09 mole), and methanesulfonic acid (1.20 g) are stirred at 95° C. in a flask equipped with a Dean Stark distillation receiver and a nitrogen sparge inlet. Over 4 hours 44 g of methanol (65% of theoretical) are collected in the receiver. PM Acetate (60.0 g, Dow Chemical Co.) is added and the temperature is increased to 115° C. to collect 8 g more methanol (77% total). Dimethyl ethanolamine (1.20 g) is added to neutralize the acid catalyst, and sufficient PM Acetate (150 g) is added to achieve a Z1 Gardner-Holdt viscosity. The resulting pale yellow resin is measured at 78.4% total nonvolatiles (110° C., 60 minutes). The approximate formula is:

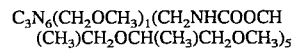
$C_3N_6(CH_2OCH_3)_1(CH_2NHCOOCH(CH_3)CH_2OCH(CH_3)CH_2OCH_3)_5$

Gel permeation chromatography shows a uniform distribution of oligomeric material (about 80%, Mw 4270) and a single peak corresponding to monomeric material.

EXAMPLE 12

Reaction Product of 5 Moles of 3-Methoxy-3-methylbutyl Carbamate with 1 Mole of Hexamethoxymethylmelamine Oligomeric hexamethoxymethylmelamine (60.0 g, 0.15 mole), 3-methoxy-3-methylbutyl carbamate (125.0 g, 0.77 mole), and methanesulfonic acid (0.37 g) are stirred at 100° C. in a flask equipped with a Dean Stark distillation receiver and a nitrogen sparge inlet. Over 1 hour 19 g of methanol (79% of theoretical) are collected in the receiver. Dimethyl ethanolamine (0.37 g) is added to neutralize the acid catalyst followed by sufficient 3-methoxy-3-methyl-1-butanol (40 g, Ken Seika Corp.) to achieve a Z2 Gardner-Holdt viscosity. The resulting clear, colorless resin is measured at 76.6% total nonvolatiles (110° C., 60 minutes). The approximate formula is:

$C_3N_6(CH_2OCH_3)_1(CH_2NHCOOCH_2CH_2C(CH_3)_2OCH_3)_5$

EXAMPLE 13

Reaction Product of 3.5 Moles of Methoxypropyl Carbamate with % Mole of Dimethoxymethyldiethoxymethylbenzoguanamine Oligomeric dimethoxymethyldiethoxymethylbenzoguanamine (250.0 g, 0.65 mole, American Cyanamid Co., CYMEL 1123), methoxymethyl carbamate (260.0 g, 1.95 mole), and methanesulfonic acid (1.00 g) are stirred at 100° C. in a flask equipped with a Dean Stark distillation receiver and a nitrogen sparge inlet. Over 2.5 hours 59 g of a methanol/ethanol mixture (78% of theoretical) are collected in the receiver. PM Acetate (100.0 g) is added and the temperature is increased to 115° C. to collect 5 g more distillate. Dimethyl ethanolamine (1.00 g) is added to neutralize the acid catalyst. Sufficient PM Acetate (75.0 g) is added to achieve a Gardner-Holdt viscosity of Z1. The resulting clear, yellow resin (575 g) is measured at 66.5% total nonvolatiles (110° C., 60 minutes). Gas chromatographic analysis shows <2% residual carbamate. The approximate formula is:

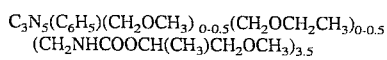

$C_3N_5(C_6H_5)(CH_2OCH_3)_{0-0.5}(CH_2OCH_2CH_3)_{0-0.5}(CH_2NHCOOCH(CH_3)CH_2OCH_3)_{3.5}$

Gel permeation chromatography shows a uniform distribution of oligomeric material (about 70%, Mw 2357) and a single peak corresponding to monomeric material.

EXAMPLE 14

Reaction Product of 3 Moles of Phenoxypropyl Carbamate with 1 Mole of Hexamethoxymethylmelamine in Excess Butanol Oligomeric hexamethoxymethylmelamine (180.0 g, 0.46 mole), phenoxypropyl carbamate (250.0 g, 1.38 mole), n-butanol (300.0 g, 4.0 mole), and dodecylbenzenesulfonic acid (0.86 g, 70%) are stirred at 100° C. in a flask equipped with a Dean Stark distillation receiver and a nitrogen sparge inlet. Over 5 hours 124 g of a methanol/butanol mixture are collected in the receiver. Dimethylethanolamine (1.0 g) is added to the neutralize the acid catalyst, and 44 g of butanol are stripped under reduced pressure (100–200 mm Hg). The resulting clear, pale yellow resin is measured at an X Gardner-Holdt viscosity and 84.5% total nonvolatiles (110° C., 60 minutes). The approximate formula is:

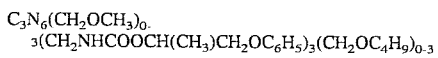

$C_3N_6(CH_2OCH_3)_{0.3}(CH_2NHCOOCH(CH_3)CH_2OC_6H_5)_3(CH_2OC_4H_9)_{0.3}$

EXAMPLE 15

Reaction Product of 3 Moles of Butyl Carbamate and 3 Moles of Methoxypropyl Carbamate with 1 Mole of Hexamethoxymethylmelamine Oligomeric hexamethoxymethylmelamine (109.0 g, 0.43 mole), butyl carbamate (153.0 g, 1.3 mole), methoxypropyl carbamate (175.0 g, 1.3 mole), and methanesulfonic acid (1.0 g) are stirred at 100° C. in a flask equipped with a Dean Stark distillation receiver and a nitrogen sparge inlet. Over 4 hours 68 g of methanol (82% of theoretical based upon the number of moles of carbamate present) are collected in the receiver. Dimethylethanolamine (1.0 g) is added to neutralize the acid catalyst and sufficient PM Acetate (110 g) is added to achieve a Gardner-Holdt viscosity of Z-. The resulting clear colorless resin is measured at 82.6% total nonvolatiles (110° C., 60 minutes). The approximate formula is:

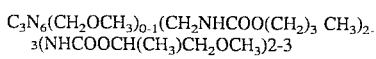

$C_3N_6(CH_2OCH_3)_{0.1}(CH_2NHCOO(CH_2)_3 CH_3)_{2-3}(NHCOOCH(CH_3)CH_2OCH_3)_{2-3}$

EXAMPLE 16

Reaction Product of 5 Moles of Methoxypropyl Carbamate with 1 Mole of Monomeric Hexamethoxymethylmelamine at Reduced Pressure Monomeric hexamethoxymethylmelamine (195.0 g, 0.5 mole, American Cyanamid Co. CYMEL 300), methoxypropyl carbamate (333.3 g, 2.5 mole), and methanesulfonic acid (1.2 g) are stirred in a flask equipped with a vacuum distillation head and purged with dry nitrogen. The temperature is maintained at 85° C. for 1 hour at which time the pressure is reduced to 200 mm Hg. Over 4 hours the pressure is gradually decreased to 50 mm Hg. At this time gas chromatographic analysis showed <2% residual carbamate, and sufficient PM Acetate (150 g) was added to achieve a Z- Gardner-Holdt viscosity. The resulting clear resin was measured at 68.8% total nonvolatiles (110° C., 60 minutes).

EXAMPLE 17

Reaction Product of 5 Moles of 2-Hexyloxyethyl Carbamate with 1 Mole of Hexamethoxymethylmelamine Oligomeric hexamethoxymethylmelamine (125.0 g, 0.32 mole), hexyloxyethyl carbamate (300.0 g, 1.59 mole), and p-toluenesulfonic acid (0.9 g) are stirred at 100° C. in a flask equipped with a Dean Stark distillation receiver and a nitrogen sparge inlet. Over 6 hours 50 g of methanol are collected in the receiver at which time PM Acetate (90 g) are added. The temperature is increased to 115° C. for 2 hours and more methanol is collected. Dimethylethanolamine (0.5 g) is added to neutralize the acid catalyst. The resulting clear, yellow resin is measured at 66.8% total nonvolatiles (110° C., 60 minutes) with a Gardner-Holdt viscosity of X. The approximate formula is:

$C_3N_6(CH_2OCH_3)_{1.2}(CH_2ONHCOOCH_2CH_2O(CH_2)_5CH_3)_{4.5}$

EXAMPLE 18

Reaction Product of 3 Moles of Methoxypropyl Carbamate and 3 Moles of Diethylene Glycol Butyl Ether Carbamate with 1 Mole Of Hexamethoxymethylmelamine Oligomeric hexamethoxymethylmelamine (129.0 g, 0.33 mole), methoxypropyl carbamate (133.0 g, 1.0 mole), diethylene glycol butyl ether carbamate (290.0 g, 70% in butyl CARBITOL, 1.0 mole), and methanesulfonic acid (1.1 g) are stirred at 110° C. in a flask equipped with a Dean Stark distillation receiver and a nitrogen sparge inlet. Over 3 hours 58 g of methanol (90% of theoretical based upon the number of moles of carbamate present) are collected in the receiver. Dimethylethanolamine (1.1 g) is added to neutralize the acid catalyst. The resulting clear, pale yellow resin is measured at 73.1% total nonvolatiles (110° C., 60 minutes) with a Gardner-Holdt viscosity of U+. The approximate formula is:

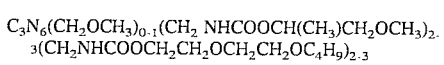

$C_3N_6(CH_2OCH_3)_{0.1}(CH_2 NHCOOCH(CH_3)CH_2OCH_3)_{2-3}(CH_2NHCOOCH_2CH_2OCH_2CH_2OC_4H_9)_{2-3}$

EXAMPLE 19

Reaction Product of Ethylene Glycol 2-Ethylhexyl Ether Carbamate, Diethylene Glycol 2-Ethylhexyl Ether Carbamate and 2-Butoxyethanol with 1 Mole of Hexamethoxymethylmelamine Oligomeric hexamethoxymethylmelamine (123.0 g, 0.32 mole), a mixture of ethylene and diethylene glycol 2-ethylhexyl ether carbamates (300.0 g, 1.26 equivalents, carbamate of EKTASOLVE EEH, Eastman Chemical Co.), 2-butoxyethanol (75.0 g, 0.63 mole), and methanesulfonic acid (1.0 g) are stirred at 100° C. in a flask equipped with a Dean Stark distillation receiver and a nitrogen sparge inlet. Over 4 hours 48 g of methanol (80% of theoretical) are collected in the receiver at which time dimethylethanolamine (1.0 g) is added to neutralize the acid catalyst. Sufficient 2-butoxyethanol (70 g) is added to achieve a Gardner-Holdt viscosity of Z. The resulting clear, pale yellow resin is measured at 77.7% total nonvolatiles (110° C., 60 minutes). The approximate formula is:

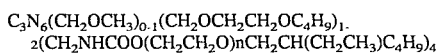

$C_3N_6(CH_2OCH_3)_{0.1}(CH_2OCH_2CH_2OC_4H_9)_{1.2}(CH_2NHCOO(CH_2CH_2O)nCH_2CH(CH_2CH_3)C_4H_9)_4$ n=1 or 2.

EXAMPLE 20

Reaction Product of 3.5 Moles of Diethylene Glycol Butyl Ether Carbamate with 1 Mole of Dimethoxymethyldiethoxymethylbenzoguanamine Oligomeric dimethoxymethyldiethoxymethylbenzoguanamine (150.0 g, 0.39 mole, American Cyanamid Co., CYMEL 1123), diethylene glycol butyl ether carbamate (280.0 g, 1.37 mole), diethylene glycol monobutyl ether (120.0 g), and methanesulfonic acid (1.5 g) are stirred at 100° C. in a flask equipped with a Dean Stark distillation receiver and a nitrogen sparge inlet. Over 6 hours 40 g of methanol are collected in the receiver at which time dimethylethanolamine (1.5 g) is added to neutralize the acid catalyst. The resulting yellow resin is measured at 65.9% total nonvolatiles with a Gardner-Holdt viscosity of H. The approximate formula is:

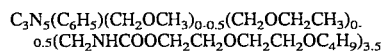

$C_3N_5(C_6H_5)(CH_2OCH_3)_{0-0.5}(CH_2OCH_2CH_3)_{0-0.5}(CH_2NHCOOCH_2CH_2OCH_2CH_2OC_4H_9)_{3.5}$

COMPARATIVE EXAMPLE 1

Reaction Product of 5 Moles of Methyl Carbamate with 1 Mole of Hexamethoxymethylmelamine (see U.S. Pat. No. 4,710,542)

Oligomeric hexamethoxymethylmelamine (260.0 g, 0.66 mole), methyl carbamate (250.0 g, 3.33 mole), and methanesulfonic acid (1.0 g) are stirred at 100° C. in a flask equipped with a Dean Stark distillation receiver and a nitrogen sparge inlet. After about 20 minutes the contents became extremely viscous and difficult to dissolve. Methoxypropanol (200 g) was added and methanol (100 g, 95% of theoretical) was removed. Dimethylethanolamine (1.0 g) was added to neutralize the acid catalyst, and sufficient methoxypropanol was removed at reduced pressure to achieve a Gardner-Holdt viscosity of Z. The resulting white, opaque resin is measured at 82.3% total nonvolatiles and is incompatible with a variety of organic solvents and water. Gas chromatographic analysis shows <2% residual carbamate.

COMPARATIVE EXAMPLE 2

Reaction Product of 5 Moles of Hydroxypropyl Carbamate with 1 Mole of Hexamethoxymethylmelamine Due to the fact that when this reaction is run neat or in the presence of a nonreactive solvent (i.e. toluene), as generally described in U.S. Pat. No. 4,708,984, gelation occurs within 2 hours at 85° C., the procedure has been amended. Oligomeric hexamethoxymethylmelamine (200.0 g, 0.51 mole), β-hydroxy-ethyl carbamate (305.0 g, 2.56 mole), methanol (100 g), and p-toluenesulfonic acid (1.5 g) are heated to reflux (72° C.) in a flask fitted with a vacuum distillation receiver. The disappearance of hydroxypropyl carbamate is monitored by gas chromatography. After 10 hours at reflux, the pressure is reduced in stages to 100 mm Hg to remove the methanol. Dimethylethanolamine (1.5 g) is added to neutralize the acid catalyst, and sufficient methoxypropanol (150 g) is added to achieve a Gardner-Holdt viscosity of Z2. The resulting clear, pale yellow resin is measured at 77.3% total nonvolatiles (110° C., 60 minutes). The approximate formula is:

$C_3N_6(CH_2OCH_3)(CH_2NHCOOCH_2CH(CH_3)OH)_5$

Gel permeation chromatography shows a fairly uniform distribution of oligomeric material (about 70%, Mw 2523) and a single peak corresponding to monomeric material.

COMPARATIVE EXAMPLE 3

Reaction Product of 6 Moles of 2-Methoxyethyl Carbamate with 1 Mole of Hexamethoxymethylmelamine (see Organic Coatings Science and Technology, XV, 379 (1989))

Oligomeric hexamethoxymethylmelamine (132.3 g, 0.34 mole), 2-methoxyethyl carbamate (200.0 g, 1.68), and methanesulfonic acid (0.63 g) are stirred at 100° C. in a flask equipped with a Dean Stark distillation receiver and a nitrogen sparge inlet. After 30 minutes the contents became very viscous and began to foam, so PM Acetate (50 g) was added. Over 3 hours 68 g of methanol (80% of theoretical) are collected in the receiver at which time dimethylethanolamine (0.63 g) is added to neutralize the acid catalyst. Sufficient PM Acetate (25 g) is added to achieve a Gardner-Holdt viscosity of Z. The resulting clear, yellow resin is measured at 66.6% total nonvolatiles (110° C., 60 minutes). The approximate formula is:

$C_3N_6(CH_2OCH_3)(CH_2NHCOOCH_2CH_2OCH_3)_5$

COMPARATIVE EXAMPLE 4

Reaction Product of 5 Moles of Octyl Carbamate with 1 Mole of Hexamethoxymethylmelamine (see U.S. Pat. No. 4,710,542)

Oligomeric hexamethoxymethylmelamine (113.0 g, 0.29 mole), n-octyl carbamate (250.0 g, 1.49 mole), and methanesulfonic acid (1.0 g) are stirred at 100° C. in a flask equipped with a Dean Stark distillation receiver and a nitrogen sparge inlet. Over 6 hours 30 g of methanol (65% of theoretical) are collected in the receiver at which time dimethylethanolamine (1.0 g) is added to neutralize the acid catalyst. The resulting white opaque resin is measured at 78.1% total nonvolatiles (110° C., 60 minutes) with a Gardner-Holdt viscosity of X. The resin became extremely viscous with time.

In the following examples, alkoxyalkylcarbamylmethylated triazines of this invention are formulated into curable compositions and evaluated as coatings.

EXAMPLE 21

A black paint was formulated from a methoxypropyl carbamate functional melamine crosslinker such as described in Example 1 (152 g), a cyclohexyl methacrylate functional acrylic polyol such as ACRYSET® UW-2818HS1 (235 g, Nippon Shokubai, hydroxyl value= 70), dibutyltin dilaurate (3.0 g), an ester/alcohol solvent blend (119 g, PM Acetate, isopropanol), and a carbon black millbase with a P/B ratio of 0.05. The resulting paint had an applied viscosity of 30" (#2 Zahn Cup, 77° F. ), a density of 8.6 lb/gal, and 54.4% total theoretical nonvolatiles. It was applied via conventional air spray over steel panels with a cured elastomeric primer and baked at 390°–400° F. for 10 minutes. The properties of the cured coating are reported in Table 1 below.

EXAMPLE 22

An indian red paint was formulated from a diethylene glycol butyl ether carbamate functional melamine crosslinker such as described in Example 10 (140 g), a hydroxyl functional acrylic such as ACRYSET® UW-2818HS1 (173 g), dibutyltin dilaurate (2.4 g), an ester/ alcohol solvent blend as in Example 21 (101 g), and an iron oxide millbase with a P/B ratio of 0.40. The resulting paint had an applied viscosity of 30" (#2 Zahn Cup, 77° F. ), a density of 8.6 lb/gal, and 61.4% total theoretical nonvolatiles. It was applied via conventional air spray over steel panels with a cured elastomeric primer and baked at 390°–400° F. for 10 minutes. The properties of the cured coating are reported in Table 1 below.

EXAMPLE 23 (COMPARATIVE)

As a comparative example, a clear coating composition was formulated from a methyl carbamate functional melamine crosslinker such as described in Comparative Example 1 (105 g), a hydroxyl functional acrylic such as ACRYSET® UW2818HS1 (175 g), dibutyltin dilaurate (2.0 g), and an ester/alcohol blend (100 g). The resulting formulation was hazy and appeared to have compatibility problems. It had a measured viscosity of 30" (#2 Zahn Cup, 77° F. ) and 58% total theoretical nonvolatiles. It was drawn down over primed steel panels and baked at 400° F. for 10 to 20 minutes. The clear coating did not give a well cured film, so many of the physical properties of the cured coating could not be measured. What properties could be measured are reported in Table 1 below.

TABLE I

| PROPERTIES | 21 | 22 | 23 |
|---|---|---|---|
| DFT (Dry Film Thickness, mil) | 1.2 | 1.2 | 1.2 |
| 60° Gloss[1] | 90 | 64 | — |
| Pencil Hardness[2] | H | H | <6B |
| MEK Double Rubs[3] | 100+ | 100+ | 10 |
| Impact: Direct[4] | 60+ | 60+ | — |
| Impact: Reverse[4] (RI) | 60+ | 60+ | — |
| Adhesion[5]: 30' Boiling Water (BWT) | 5 | 5 | — |
| Adhesion: 30' BWT + 30 in/lb RI | 4+ | 4+ | — |
| Adhesion: 24 hr H₂O Soak | 5 | 5 | — |
| Detergent Resistance[6] | Excellent | Excellent | — |
| 10% Hydrochloric Acid Resistance[7] | Excellent | Excellent | — |
| 5% Salt Spray: 3000 hr.[8] | Excellent | Excellent | — |
| QUV: 3000 hr (% gloss retention)[9] | >90% | >90% | — |

[1]Specular Gloss measured in accordance with ASTM D523-89.
[2]Pencil Hardness was determined by taking sharpened pencils of increasing hardness (6B to 5H) and attempting to etch a scribe mark in the coating. The next softest pencil which will etch the coating is reported as the pencil hardness (ASTM D-3363).
[3]Number of rubs back and forth (1 double rub) with a cloth saturated with methyl ethyl ketone using normal hand pressure required to remove the coating from the substrate. Limit of the test is 100 double rubs.
[4]Impact Resistance was measured with a Gardner Impact Tester (4 lb, ⅝" ball). The results are reported in inch-pounds, 0.10 inch deformation, no tape-off.
[5]Adhesion: Panel was crosshatched at 1/16" and evaluated with Scotch 610 tape. Reported on a scale of 0 to 5 (best).
[6]Detergent Resistance: 72 hour immersion in 3% solution of detergent in distilled water at 100° F.
[7]10% Hydrochloric Acid Resistance: 15 minute covered spot test.
[8]Salt Spray: 3000 hour (scribed) at 95° F. and 5% salt solution (ASTM D-117).
[9]QUV Exposure is determined by exposing the coated panels to alternating cycles of U.V. light and condensing humidity in a Q-U-V Accelerated Weathering Tester manufactured by the Q-Panel Co. The U.V. light is generated with a UVB313 lamp (320–280 nm). The temperature of the light cycle is 70° C. The temperature of the condensing humidity is 50° C.

EXAMPLE 24

A musket brown waterborne dispersion was prepared using a crosslinker prepared from 5 moles of butoxypropyl carbamate and 1 mole of hexamethoxymethylmelamine such as that of Example 4. A pigment grind was prepared from a solventborne acrylic grind vehicle containing styrene, butyl acrylate, methyl methacrylate, and acrylic acid (7.9 g, 40% solids, acid value=30), butyl CARBITOL® (1.5 g), ethylene glycol (5.3 g), triethylamine (0.5 g), and 16.6 g of a pigment mixture of carbon black, iron oxide, light sienna, and titanium dioxide (Weight Ratio 1:1.6:2.5:2.3). To this, the carbamate/melamine crosslinker (15.9 g) was added at high shear to form the grind paste. The paste was then added with agitation to an acrylic emulsion containing methyl methacrylate, butyl acrylate, acrylic acid, and hydroxyethyl acrylate (170.0 g, 50% solids, hydroxyl value= 10) and appropriate surfactants. The resulting paint had a P/B ratio of 0.17 at 48.0% total nonvolatiles. It was applied over elastomerically primed aluminum panels and baked for a 35 second dwell at 520° F. (to 420° F. peak metal temperature). The properties of the cured coating are reported in Table 2 below.

EXAMPLE 25

A musket brown waterborne dispersion was prepared using a crosslinker prepared from 6 moles of diethylene glycol butyl ether carbamate and 1 mole of hexamethoxymethylmelamine such as that of Example 10. The carbamate/ melamine crosslinker (12.8 g) was used to prepare the pigment grind in a manner similar to that of Example 24. The resulting paste was added with agitation to 170.0 g of the acrylic emulsion described in Example 24. The resulting paint had a P/B ratio of 0.17 at 47.5% total nonvolatiles. It was applied over elastomerically primed aluminum panels and baked for a 35 second dwell at 520° F. (to 420° F. peak metal temperature). The properties of the cured coating are reported in Table 2 below.

TABLE 2

| PROPERTIES | 24 | 25 |
| --- | --- | --- |
| Pencil Hardness | HB | HB |
| MEK Double Rubs | 100 | 100 |
| T-Bend Adhesion[1] | | |
| No Pick | 2T | 2T |
| No Crack | 3T | 2T |

[1]The film was evaluated for cracking and adhesion loss after the coated panel was bent over itself to varying degrees. The film is observed at the edges for cracking and for removal of the film when a piece of adhesive tape is pressed down onto the edge and then quickly ripped from the film. The value is assigned at the lowest point where cracking or adhesion loss is not observed. A 3T rating means that the diameter of the bend is 3 times the thickness of the panel. A 2T bend means that the diameter of the bend is 2 times the thickness and so on. A 0T bend means that the panel is bent back over itself and compressed flat.

EXAMPLE 26

A high solids clear coating composition was formulated from a crosslinker prepared from 3 moles of methoxypropyl carbamate, 3 moles of butyl carbamate, and 1 mole of hexamethoxymethylmelamine as described in Example 15 (46.0 g), a low molecular weight polyester prepared from sebacic acid and propylene oxide (23.2 g, hydroxyl value= 228, 99.8% solids), dibutyltin dilaurate (0.9 g), and PM Acetate (5.0 g). The resulting clear had an applied viscosity of 20 seconds (#4 Zahn Cup) and was drawn down over unprimed steel panels. The films were baked at 350° F. for 20 minutes. The properties of the cured coating are reported in Table 3 below.

EXAMPLE 27

A high solids clear coating composition was formulated from a crosslinker prepared from 3 moles of butoxyethyl carbamate and 1 mole of hexamethoxymethylmelamine as described in Example 7 (38.2 g), the polyester used in Example 26 (23.2 g), dibutyltin dilaurate (0.92 g), and PM Acetate (7.6 g). The resulting clear had an applied viscosity of 20 seconds (#4 Zahn Cup) and was drawn down over unprimed steel panels. The films were baked at 350° F. for 20 minutes. The properties of the cured coating are reported in Table 3 below.

EXAMPLE 28

A high solids clear coating composition was formulated from a crosslinker prepared from 3.5 mole of methoxypropyl carbamate and 1 mole of dimethoxymethyldiethoxymethylbenzoguanamine as described in Example 13 (39.0 g), the polyester used in Example 26 (23.2 g), dibutyltin dilaurate (0.90 g), and PM Acetate (5.2 g). The resulting clear had an applied viscosity of 20 seconds (#4 Zahn Cup) and was drawn down over unprimed steel panels. The films were baked at 350° F. for 20 minutes. The properties of the cured coating are reported in Table 3 below.

EXAMPLE 29 (COMPARATIVE)

As a comparative example, a clear coating composition was formulated from the methoxyethyl carbamate functional crosslinker described in Comparative Example 3 (49.5 g), the polyester used in Example 26 (23.2 g), dibutyltin dilaurate (0.95 g), and PM Acetate. The resulting clear had an applied viscosity of 20 seconds (#4 Zahn Cup) and was drawn down over unprimed steel panels. The films were baked at 350° F. for 20 minutes. The properties of the cured coating are reported in Table 3 below.

TABLE 3

| PROPERTIES | 26 | 27 | 28 | 29 |
| --- | --- | --- | --- | --- |
| % Solids | 80.9 | 78.6 | 76.3 | 71.0 |
| DFT (mils) | 1.3 | 1.2 | 1.2 | 1.15 |
| Pencil Hardness | H | F-H | 2B | F |
| MEK Double Rubs | 100 | 100 | 100 | 100 |
| Impact: Direct | >160 | 100 | 100 | 160 |
| Impact: Reverse | >160 | 90 | 90 | 140 |

EXAMPLE 30

An aqueous dispersion of a cationic resin and the crosslinker of Example 8 was prepared from the following ingredients:

| Ingredients | Parts by Weight |
| --- | --- |
| EPON 828 | 3850.2 |
| Bisphenol A/Ethylene Oxide Adduct (1/6 molar ratio) | 1370.7 |
| Bisphenol A | 1116.2 |
| Methyl Isobutyl Ketone | 333.5 |
| Benzyldimethylamine | 5.6 |
| Benzyldimethylamine | 15.2 |
| Diketamine[1] | 399.0 |
| N-Methylethanolamine | 345.3 |
| Methyl Isobutyl Ketone | 564.3 |

[1]Diketamine derived from diethylenetriamine and methyl isobutyl ketone (73% solids in methyl isobutyl ketone).

The EPON 828 (diglycidyl ether of bisphenol A available from Shell Chemical Co.), bisphenol A/ethylene oxide adduct, bisphenol A and methyl isobutyl ketone (first portion) were charged to a reaction vessel and heated under a nitrogen atmosphere to 140° C. The first portion of the benzyldimethylamine was added, and the reaction mixture was allowed to exotherm while any water present was removed azeotropically.

The reaction mixture was cooled to 160° C., held for ½ hour, cooled to 145° C., and the second portion of benzyldimethylamine added. The reaction was held until a reduced Gardner-Holdt viscosity (50% resin solids in 2-methoxypropanol) of R to S was obtained. At this point the diketamine and N-methylethanolamine were added in succession. The mixture was allowed to exotherm and then a temperature of 125° C. was established. After 1 hour at 125° C., the second portion of methyl isobutyl ketone was added to the reaction mixture.

To 685.5 g of the resin as described above was added 400 g of the crosslinker of Example 8. This mixture was held at 110° C. for 15 minutes at which time sulfamic acid (29.3 g) and deionized water (29.3 g) were added. The temperature was maintained at 60–65° C., and the mixture was reduced in stages with deionized water to 33.0%. The resin possessed the following measured properties: MEq Acid=0.109, MEq Base=0.215, Particle Size=1770Å, Mw=21936.

A cationic electrodeposition bath was formulated with the aqueous dispersion prepared above and other ingredients as follows:

| Ingredient | Parts by Weight |
| --- | --- |
| Aqueous Dispersion | 1851.2 |
| Flow Control Agent[1] | 119.1 |
| Plasticizer[2] | 41.7 |
| Pigment Paste[3] | 221.5 |
| Deionized Water | 1566.5 |

[1]The flow control agent is a polyepoxide-polyalkylenediamine adduct prepared as generally described in Example A of U.S. Pat. No. 4,933,056.
[2]Plasticizer available from Rohm and Haas Company as PARAPLEX WP-1.
[3]Pigment paste available from PPG Industries, Inc. as E-6064, containing 27.2% titanium dioxide, 1.4% carbon black, 15.9% aluminum silicate, 5.7% basic lead silicate, and 3.8% dibutyltin oxide.

The aqueous dispersion, flow control agent, and plasticizer were mixed together for 30 minutes. The pigment paste was then added with agitation, followed by the deionized water. The electrodeposition bath had a solids content of 22% and a pH of 6.97.

Phosphated steel panels were electrodeposited in the bath at 200 volts to a thickness of 1.2 mils. The coatings were cured at 360° F. (182° C.) for 30 minutes and were resistant to 100 acetone double rubs. The cured films had good humidity and chip resistance.

What is claimed is:

1. A curable composition comprising:
   (a) the triazine compound selected from the group consisting of:
   (i) a triaminotriazine compound of the formula $C_3N_6(CH_2OR)_{6-x}(CH_2NHCOOR')_x$;
   ii) a benzoguanamine compound of the formula $C_3N_5(C_6H_5)(CH_2-OR)_{4-y}(CH_2NHCOOR')_y$;
   (iii) an oligomer of (i) or (ii) including mixtures thereof wherein the R and R' are independently radicals derived from monoalkyl ethers of alkylene glycols having at least 4 carbon atoms and monoaryl ethers of alkylene glycols having at least 8 carbon atoms; alone or combined with hydrogen or alkyl groups having 1 to 20 carbon atoms; x is in the range of from about 2 to about 6 and y is in the range of from about 2 to about 4;
   (b) an active hydrogen-containing polymeric material.

2. The curable composition of claim 1 in which the active hydrogen-containing material is a polymeric material in which the active hydrogens are selected from the group consisting of carboxylic acid, hydroxy, amino, amido, thiol or mixtures of such groups.

3. The curable composition of claim 1 in which the active hydrogen-containing polymeric material is selected from the group consisting of hydroxy functional acrylic polymers, hydroxy functional polyesters, hydroxy functional polyurethanes, hydroxy functional epoxy polymers and hydroxy functional epoxy-amine reaction product polymers including mixtures thereof.

4. The curable composition of claim 1 which includes a cure catalyst.

5. The curable composition of claim 4 in which the cure catalyst is selected from the class consisting of a tin catalyst alone or in combination with an acid catalyst.

6. The curable composition of claim 1 in which components (a) and (b) are dispersed or solubilized in water or mixtures of water and organic solvent.

7. The curable composition of claim 1 in which (a) and (b) are present in amounts of at least 5% by weight based on total weight of the composition.

8. The curable composition of claim 1 in which the weight ratio of (a) to (b) is from 5–40 to 95–60.

* * * * *